(12) United States Patent
Ha et al.

(10) Patent No.: US 10,953,387 B2
(45) Date of Patent: Mar. 23, 2021

(54) CALCIUM SALTS-SUPPORTED METAL CATALYST, METHOD FOR PREPARING THE SAME, AND METHOD FOR HYDRODEOXYGENATION REACTION OF OXYGENATES USING THE SAME

(71) Applicant: KOREA INSTITUTE OF SCIENCE AND TECHNOLOGY, Seoul (KR)

(72) Inventors: Jeong-Myeong Ha, Seoul (KR); Adid Adep Dwiatmoko, Seoul (KR); Jae Wook Choi, Seoul (KR); Dong Jin Suh, Seoul (KR); Jungho Jae, Seoul (KR); Young Hyun Yoon, Seoul (KR); Kwang Ho Kim, Seoul (KR)

(73) Assignee: KOREA INSTITUTE OF SCIENCE AND TECHNOLOGY, Seoul (KR)

( * ) Notice: Subject to any disclaimer, the term of this patent is extended or adjusted under 35 U.S.C. 154(b) by 0 days.

(21) Appl. No.: 16/292,324

(22) Filed: Mar. 5, 2019

(65) Prior Publication Data
US 2019/0381484 A1    Dec. 19, 2019

(30) Foreign Application Priority Data

Jun. 18, 2018 (KR) .......................... 10-2018-0069705

(51) Int. Cl.
 *B01J 23/46* (2006.01)
 *B01J 37/08* (2006.01)
 (Continued)

(52) U.S. Cl.
 CPC ......... *B01J 23/462* (2013.01); *B01J 37/0201* (2013.01); *B01J 37/08* (2013.01);
 (Continued)

(58) Field of Classification Search
 CPC ... B01J 23/02; B01J 23/40; B01J 23/46; B01J 23/462; B01J 23/464; B01J 23/58;
 (Continued)

(56) References Cited

U.S. PATENT DOCUMENTS 3,193,584 A * 7/1965 Kreidl ..................... C07B 31/00
                                                                568/579
3,513,109 A * 5/1970 Stiles ................... B01J 37/0234
                                                                502/241
(Continued)

FOREIGN PATENT DOCUMENTS

JP   2012115725 A   6/2012
JP   2013185130 A   9/2013
(Continued)

OTHER PUBLICATIONS

Korean Notice of Allowance for corresponding Korean Patent Application No. 10-2018-0069705 dated Feb. 10, 2020, citing the above references.

*Primary Examiner* — Patricia L. Hailey
(74) *Attorney, Agent, or Firm* — Cantor Colburn LLP

(57) ABSTRACT

Disclosed herein are a calcium salts-supported metal catalyst, a method for preparing the same, and a method for the hydrodeoxygenation reaction of oxygenates using the same. The catalyst, in which a metal catalyst is supported on a carrier of a calcium salt, for example, calcium carbonate, has the effect of increasing the efficiency of hydrodeoxygenation reaction of oxygenates.

8 Claims, 4 Drawing Sheets

(51) Int. Cl.
*B01J 37/02* (2006.01)
*C07C 1/20* (2006.01)
*B01J 37/18* (2006.01)
*C07C 13/18* (2006.01)

(52) U.S. Cl.
CPC ............... *C07C 1/20* (2013.01); *B01J 37/18* (2013.01); *C07C 13/18* (2013.01); *C07C 2523/46* (2013.01); *C07C 2601/14* (2017.05)

(58) Field of Classification Search
CPC . B01J 23/75; B01J 23/755; B01J 23/78; B01J 37/0201; B01J 37/08; B01J 37/18; C07C 1/20; C07C 13/18; C07C 2523/46; C07C 2601/14
USPC ............... 502/217, 226, 325, 326, 328, 340
See application file for complete search history.

(56) References Cited

U.S. PATENT DOCUMENTS

| | | | |
|---|---|---|---|
| 8,669,400 B2 * | 3/2014 | Johnston | B01J 37/0203 568/885 |
| 2003/0119666 A1 * | 6/2003 | Kadowaki | B01J 23/75 502/305 |
| 2010/0019191 A1 * | 1/2010 | Hoffer | C07C 29/00 252/70 |
| 2011/0087058 A1 * | 4/2011 | Harlin | B01J 31/20 585/240 |
| 2012/0330067 A1 * | 12/2012 | Devon | B01J 21/066 568/678 |
| 2013/0243687 A1 | 9/2013 | Ozaki et al. | |
| 2013/0261363 A1 * | 10/2013 | Serban | B01J 23/63 585/430 |
| 2017/0073592 A1 | 3/2017 | Nonaka et al. | |

FOREIGN PATENT DOCUMENTS

| | | | | |
|---|---|---|---|---|
| JP | 2015167936 | A | 9/2015 | |
| KR | 1020130017250 | A | 2/2013 | |
| KR | 101305907 | B1 | 9/2013 | |
| KR | 101571129 | B1 | 11/2015 | |
| KR | 1020170133092 | A | 12/2017 | |
| KR | 101827931 | B1 | 2/2018 | |
| KR | 101857187 | B1 | 5/2018 | |
| KR | 1020190006336 | A | 1/2019 | |
| KR | 1020190006385 | A | 1/2019 | |
| WO | 2010/043765 | * | 4/2010 | ............... C10G 3/00 |

* cited by examiner

CALCIUM SALTS-SUPPORTED METAL CATALYST, METHOD FOR PREPARING THE SAME, AND METHOD FOR HYDRODEOXYGENATION REACTION OF OXYGENATES USING THE SAME

BACKGROUND OF THE INVENTION

Field of the Invention

Disclosed herein are a metal catalyst supported on a calcium salt such as calcium carbonate, a method for preparing the same, and a method for the hydrodeoxygenation reaction of oxygenates using the same.

EXPLANATION ON NATIONALLY SUPPORTED RESEARCH AND DEVELOPMENT

This research has been carried out under the supervision of the Korea Institute of Science and Technology with the support of the Ministry of Trade, Industry and Energy (specialized organization for research management: Korea Institute of Energy Technology Evaluation and Planning, title of research project: Development of Catalytic Chemical Reaction Technique for High-Carbon Transport Fuelization of Furan-based Compounds Derived from Unfermented Sugar, project assignment number: 1415154087).

Description of the Related Art

Woody biomass, including wood and herbs, is presented as a potentially sustainable source of raw materials for the production of biofuels and substitute chemicals for petroleum, and these biofuels and chemicals can be obtained through thermochemical processes such as pyrolysis. Thermochemical processes including pyrolysis and liquefaction are widely studied chemical processes. Pyrolysis oils is environmentally friendly compared to fossil fuels because it can be obtained from renewable sources. However, high oxygen concentrations inhibit the direct use of this biofuel. In addition, thermal instability and difficulty in storage of bio-oils are major obstacles to the widespread use of bio-oils. In order to convert bio-oils to petroleum-like fuels, biomass pyrolysis oils must be stabilized and oxygen atoms must be removed therefrom.

Hydrodeoxygenation (HDO) reaction is one of the processes frequently used to convert biofuels to petroleum-like deoxygenated hydrocarbon fuels. The hydrodeoxygenation reaction allows to obtain an oil with significantly improved fuel properties, including stabilization and high energy density. Although there are not many actual cases of catalytic chemical conversion of biomass pyrolysis oils, systematic researches involving biomass pyrolysis oils and catalysts and using model compounds have become very active. It is well known that in the development of catalysts for hydrodeoxygenation reaction, the interaction between reactants and catalysts affects the hydrodeoxygenation reaction. Catalyst carriers can improve the catalytic activity for hydrodeoxygenation reaction depending on the state of the reaction. For example, a lot of studies on HDO reaction have been conducted for transition metal or noble metal catalysts using solid acids such as silica and alumina as the carrier. Also, in addition to these solid acid-based catalysts, MgO-supported catalysts have been applied to the hydrodeoxygenation reaction.

CITATION LIST

Patent Literature

Patent Literature 1: Korean Patent Laid-Open No. 10-2013-0017250

SUMMARY OF THE INVENTION

In one aspect, an object of the present disclosure is to provide a catalyst for the hydrodeoxygenation reaction of oxygenates.

In another aspect, an object of the present disclosure is to provide a method for preparing the catalyst for hydrodeoxygenation reaction.

In yet another aspect, an object of the present disclosure is to provide a method for the hydrodeoxygenation reaction of oxygenates using the catalyst for hydrodeoxygenation reaction.

In one aspect, the technology disclosed herein provides a catalyst for hydrodeoxygenation reaction comprising a carrier comprising a calcium salt, and a metal catalyst supported on the carrier.

In one exemplary embodiment, the calcium salt may comprise at least one selected from the group consisting of calcium chloride, calcium fluoride, calcium hydroxide, calcium carbonate, calcium nitrate, calcium acetate, calcium citrate, calcium lactate, calcium phosphate, calcium gluconate, calcium sulfate, and calcium iodate.

In one exemplary embodiment, the calcium salt may comprise calcium carbonate.

In one exemplary embodiment, the catalyst for hydrodeoxygenation reaction may remove the oxygen atoms of oxygenates.

In one exemplary embodiment, the oxygenates may be oxygen-containing hydrocarbon compounds having 5 to 20 carbon atoms.

In one exemplary embodiment, the oxygenates may comprise at least one selected from the group consisting of phenol, alcohol, aldehyde, ketone, ether, and ester.

In one exemplary embodiment, the metal catalyst may comprise at least one selected from the group consisting of nickel (Ni), cobalt (Co), copper (Cu), platinum (Pt), palladium (Pd), rhodium (Rh), and ruthenium (Ru).

In one exemplary embodiment, the metal catalyst may comprise ruthenium (Ru).

In one exemplary embodiment, the content of the metal catalyst may be 0.01 to 50% by weight based on the total weight of the catalyst for hydrodeoxygenation reaction.

In another aspect, the technology disclosed herein provides a method for preparing the catalyst for hydrodeoxygenation reaction, comprising the steps of: (1) mixing a solution of a metal catalyst precursor with a carrier comprising a calcium salt to impregnate it; and (2) firing the carrier impregnated with the solution of a metal catalyst precursor.

In one exemplary embodiment, the firing may be carried out in an air atmosphere at 100 to 500° C.

In another aspect, the technology disclosed herein provides a method for the hydrodeoxygenation reaction of oxygenates, comprising the step of applying the catalyst for hydrodeoxygenation reaction to oxygenates to remove the oxygen atoms of the oxygenates.

In one exemplary embodiment, the reaction method may comprise the steps of: introducing the catalyst for hydrodeoxygenation reaction, the oxygenate and hydrogen gas into a reactor; and heating the reactor to carry out the hydrodeoxygenation reaction of the oxygenate.

In one exemplary embodiment, the hydrogen gas may be introduced at a pressure of 10 to 100 bar at room temperature.

In one exemplary embodiment, the hydrodeoxygenation reaction may be carried out at 100 to 500° C.

The technology disclosed herein provides a catalyst for the hydrodeoxygenation reaction of oxygenates.

The metal catalyst supported on a calcium salt carrier according to the present invention increases the efficiency of hydrodeoxygenation reaction of oxygenates.

In another aspect, the technology disclosed herein provides a method for preparing the catalyst for hydrodeoxygenation reaction.

In yet another aspect, the technology disclosed herein provides a method for the hydrodeoxygenation reaction of oxygenates using the catalyst for hydrodeoxygenation reaction.

DETAILED DESCRIPTION OF THE PREFERRED EMBODIMENTS

Figure 1:
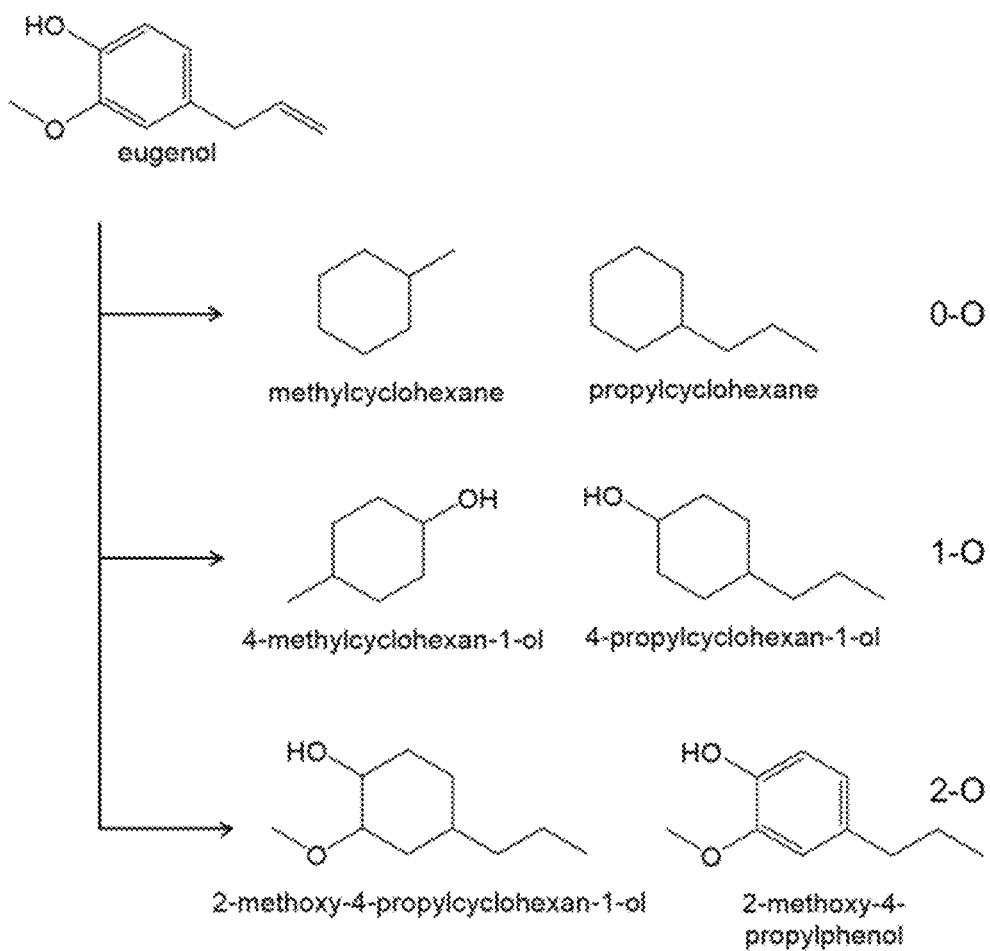
FIG. 1 shows the reactants and products of the hydrodeoxygenation reaction according to one embodiment of the present invention.
Figure 2:
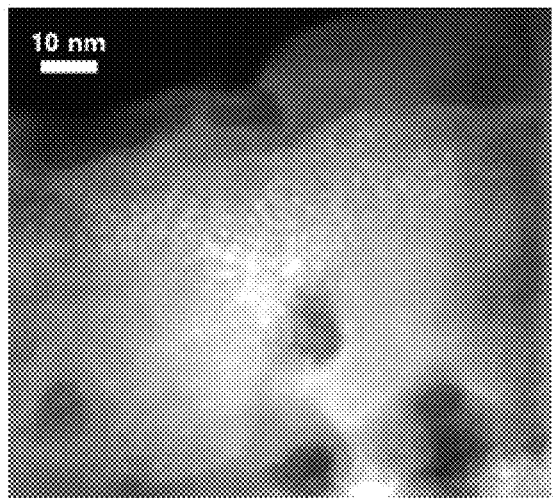
FIG. 2 is a TEM photograph of a ruthenium catalyst supported on calcium carbonate according to one embodiment of the present invention.

Hereinafter, the present invention will be described in detail.

In one aspect, the technology disclosed herein provides a catalyst for hydrodeoxygenation reaction comprising a carrier comprising a calcium salt, and a metal catalyst supported on the carrier.

In another aspect, the technology disclosed herein provides a catalyst for hydrodeoxygenation reaction comprising a carrier consisting of a calcium salt, and a metal catalyst supported on the carrier.

In one exemplary embodiment, the calcium salt may comprise at least one selected from the group consisting of calcium chloride, calcium fluoride, calcium hydroxide, calcium carbonate, calcium nitrate, calcium acetate, calcium citrate, calcium lactate, calcium phosphate, calcium gluconate, calcium sulfate, and calcium iodate.

In another aspect, the technology disclosed herein provides a catalyst for hydrodeoxygenation reaction comprising a carrier comprising calcium carbonate ($CaCO_3$), and a metal catalyst component supported on the carrier.

In another aspect, the technology disclosed herein provides a catalyst for hydrodeoxygenation reaction comprising a carrier consisting of calcium carbonate ($CaCO_3$), and a metal catalyst component supported on the carrier.

The crystallinity of the calcium carbonate carrier is not limited, and the appearance shape of the calcium carbonate carrier, such as powder or pellet, may not be limited.

In one exemplary embodiment, the catalyst for hydrodeoxygenation reaction may allow to prepare deoxygenated compounds from oxygenates.

The catalyst for hydrodeoxygenation reaction according to the present disclosure improves the reactivity of oxygenates to hydrodeoxygenation by using a calcium salt as a carrier and thereby achieves a high hydrodeoxygenation reaction efficiency.

As used herein, the term "oxygenate" refers to a compound that contains an oxygen atom within the molecular structure.

As used herein, the term "deoxygenated compound" refers to a compound obtained by removing the oxygen contained in an oxygenate. It may refer to a compound that does not contain an oxygen atom within the molecular structure.

In one exemplary embodiment, the oxygenate may comprise at least one selected from the group consisting of phenol, alcohol, aldehyde, ketone, ether, and ester.

In one exemplary embodiment, the oxygenate may be an oxygen-containing hydrocarbon compound.

In one exemplary embodiment, the oxygenate may be an oxygen-containing aromatic hydrocarbon compound.

In one exemplary embodiment, the oxygenate may have 5 to 20 carbon atoms. In another exemplary embodiment, the oxygenate may have 5 or more, 6 or more, 7 or more, 8 or more, 9 or more, 10 or more, 11 or more, 12 or more, 13 or more, 14 or more, or 15 or more carbon atoms. In another exemplary embodiment, the oxygenate may have 20 or less, 19 or less, 18 or less, 17 or less, 16 or less, 15 or less, 14 or less, 13 or less, 12 or less, 11 or less, or 10 or less carbon atoms.

In one exemplary embodiment, the oxygenate may be a degradation product produced by thermal, chemical, or biological degradation of an organic material including an organic polymer.

In one exemplary embodiment, the oxygenate may be a degradation product produced by thermal, chemical, or biological degradation of biomass including wood, herbs, and algae.

In one exemplary embodiment, the oxygenate may be obtained from pyrolysis oil of woody biomass.

In one exemplary embodiment, the oxygenate may be a lignin monomer.

In one exemplary embodiment, the oxygenate may be eugenol.

In one exemplary embodiment, the deoxygenated compound may be at least one of methyl chlorohexane and propyl chlorohexane.

In one exemplary embodiment, the metal catalyst may comprise at least one selected from the group consisting of nickel (Ni), cobalt (Co), copper (Cu), platinum (Pt), palladium (Pd), rhodium (Rh), and ruthenium (Ru).

In one exemplary embodiment, it is preferable, in terms of the hydrodeoxygenation reaction efficiency of the catalyst according to the present disclosure, that the metal catalyst comprise ruthenium (Ru).

In one exemplary embodiment, the metal catalyst may be formed from at least one metal precursor selected from the group consisting of a nickel (Ni) precursor, a cobalt (Co) precursor, a copper (Cu) precursor, a platinum (Pt) precursor, a palladium (Pd) precursor, a rhodium (Rh) precursor, and a ruthenium (Ru) precursor.

In one exemplary embodiment, the metal precursor may be at least one selected from the group consisting of a metal salt compound, a metal acetate compound, a metal halide compound, a metal nitrate compound, a metal hydroxide compound, a metal carbonyl compound, a metal sulfate compound, and a fatty acid metal salt compound.

In one exemplary embodiment, the metal precursor may be a metal chloride or a metal chlorate.

In one exemplary embodiment, the content of the metal catalyst may be 0.01 to 50% by weight based on the total weight of the catalyst for hydrodeoxygenation reaction. In another exemplary embodiment, the content of the metal catalyst may be 0.01% by weight or more, 0.1% by weight or more, 1% by weight or more, 3% by weight or more, 5% by weight or more, 7% by weight or more, or 10% by weight or more based on the total weight of the catalyst for hydrodeoxygenation reaction. In yet another exemplary embodiment, the content of the metal catalyst may be 50% by weight or less, 45% by weight or less, 40% by weight or less, 35% by weight or less, 30% by weight or less, 25% by weight or less, 20% by weight or less, 15% by weight or less, 10% by weight or less, 7% by weight or less, or 5% by weight or less based on the total weight of the catalyst for hydrodeoxygenation reaction. For example, it is preferable, in terms of the activity of hydrodeoxygenation reaction and the efficiency of the catalyst, that the content of the metal catalyst be 3 to 10% by weight based on the total weight of the catalyst for hydrodeoxygenation reaction.

In another aspect, the technology disclosed herein provides a method for preparing a catalyst for hydrodeoxygenation reaction, comprising the steps of: (1) mixing a solution of a metal catalyst precursor with a carrier comprising a calcium salt to impregnate it; and (2) firing the carrier impregnated with the solution of a metal catalyst precursor.

In one exemplary embodiment, step (1) may comprise the step of dissolving a metal catalyst precursor in ion-exchanged water and then mixing the resultant with a carrier comprising a calcium salt.

In one exemplary embodiment, step (2) may comprise the step of drying the carrier impregnated with the solution of a metal catalyst precursor and then firing and reducing it.

In one exemplary embodiment, the firing may be carried out in an air atmosphere at 100 to 500° C. In another exemplary embodiment, the firing may be carried out at a temperature of 100° C. or more, 150° C. or more, 200° C. or more, 250° C. or more, or 300° C. or more. In yet another exemplary embodiment, the firing may be carried out at a temperature of 500° C. or less, 450° C. or less, 400° C. or less, 350° C. or less, 300° C. or less, or 250° C. or less.

In one exemplary embodiment, the firing may be carried out for 1 to 10 hours.

In another aspect, the technology disclosed herein provides a method for the hydrodeoxygenation reaction of oxygenates, comprising the step of applying a catalyst for hydrodeoxygenation reaction to oxygenates to remove the oxygen atoms of the oxygenates.

In one exemplary embodiment, the reaction method may comprise the steps of: introducing the catalyst for hydrodeoxygenation reaction, the oxygenate and hydrogen gas into a reactor; and heating the reactor to carry out the hydrodeoxygenation reaction of the oxygenate.

In one exemplary embodiment, the reactor may be a batch reactor.

In one exemplary embodiment, an inert gas of nitrogen or helium may or may not be introduced into the reactor.

In one exemplary embodiment, the hydrogen gas may be introduced at a pressure of 10 to 100 bar at room temperature. In another exemplary embodiment, the hydrogen gas may be introduced at a pressure of 10 bar or more, 20 bar or more, 30 bar or more, 40 bar or more, or 50 bar or more at room temperature. In yet another exemplary embodiment, the hydrogen gas may be introduced at a pressure of 100 bar or less, 90 bar or less, 80 bar or less, 70 bar or less, 60 bar or less, or 50 bar or less at room temperature.

In one exemplary embodiment, the hydrodeoxygenation reaction may be carried out at 100 to 500° C. In another exemplary embodiment, the hydrodeoxygenation reaction may be carried out at a temperature of 100° C. or more, 150° C. or more, 200° C. or more, 250° C. or more, or 300° C. or more. In yet another exemplary embodiment, the hydrodeoxygenation reaction may be carried out at a temperature of 500° C. or less, 450° C. or less, 400° C. or less, 350° C. or less, 300° C. or less, or 250° C. or less. If the temperature is less than, for example, 100° C., there is almost no hydrodeoxygenation reaction activity. If the temperature is higher than 500° C., it is difficult to operate the reactor due to the high temperature and high pressure, and rapid deactivation of the catalyst may occur. Thus, the hydrodeoxygenation reaction of oxygenates may preferably be carried out at 200 to 500° C. or at 250 to 400° C.

Hereinafter, the present invention will be described in detail by way of examples. It will be apparent to those skilled in the art that these examples are for illustrative purposes only, and the scope of the present invention is not construed as being limited by these examples.

Example 1

In order to prepare 5% by weight of Ru/CaCO$_3$, 10.3 g of RuCl$_3$ was mixed with 50 g of ion-exchanged water and completely dissolved, and then the resultant was mixed with 95 g of calcium carbonate or other carriers. The mixture was stirred for 30 minutes, dried at 90° C. for 16 hours and then fired at 400° C. for 2 hours in an air atmosphere. Thereafter, the mixture was reduced by flowing 5% Ha/Ar mixed gas at 400° C. for 4 hours. Catalysts comprising 5% by weight of Ru were prepared by the same method using magnesium oxide (MgO), magnesium-aluminum mixed oxide (MgAlO$_x$), hydrotalcite (HT), and zirconia (ZrO$_2$) as the other carriers.

Test Example 1

Hydrodeoxygenation reaction was carried out using the catalysts prepared in Example 1 and a batch reactor. Eugenol (CAS 97-53-0) was used as a reactant. 0.003 mol of eugenol, 30 mL of n-hexadecane, and 0.05 g of a catalyst were introduced into an autoclave reactor (internal volume of about 160 mL) at room temperature, which was then filled with 50 bar of hydrogen gas at room temperature. The reactor was heated to 250° C., followed by stirring at 800 rpm for 1 hour to carry out the reaction. The reactor was cooled back to room temperature and then the liquid reaction product was analyzed.

Figure 3:
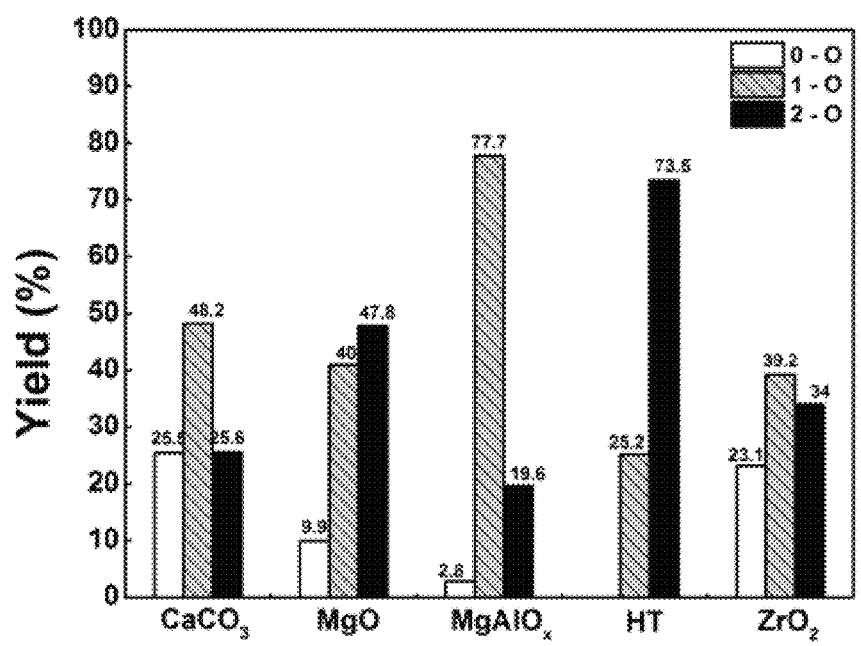
FIG. 3 compares the hydrodeoxygenation reaction results of various catalysts.

FIG. 1 shows the reactants and products of the hydrodeoxygenation reaction. A product having no oxygen atom (0-O), a product having one oxygen atom (1-0), and a product having two oxygen atoms (2-O) were obtained from eugenol, which has two oxygen atoms. As shown in FIG. 3, when CaCO$_3$ was used as the carrier, the yield of the product having two oxygen atoms (2-O) was lower and the yield of the product having no oxygen atom (0-O) was higher than the various basic carriers, including MgO, Mg—Al mixed oxide (MgAlO$_x$), hydrotalcite (HT), and zirconia (ZrO$_2$), which indicates that the carrier significantly increased the hydrodeoxygenation reaction activity. When CaCO$_3$ was used as the carrier, the yield of 1-0 was about 25% higher than the case of using a zirconia carrier, and the yield of 2-0, which did not go through hydrodeoxygenation reaction, was about 30% lower than the case of using a zirconia carrier, which indicates that the carrier increased the hydrodeoxygenation reaction efficiency.

Figure 4:
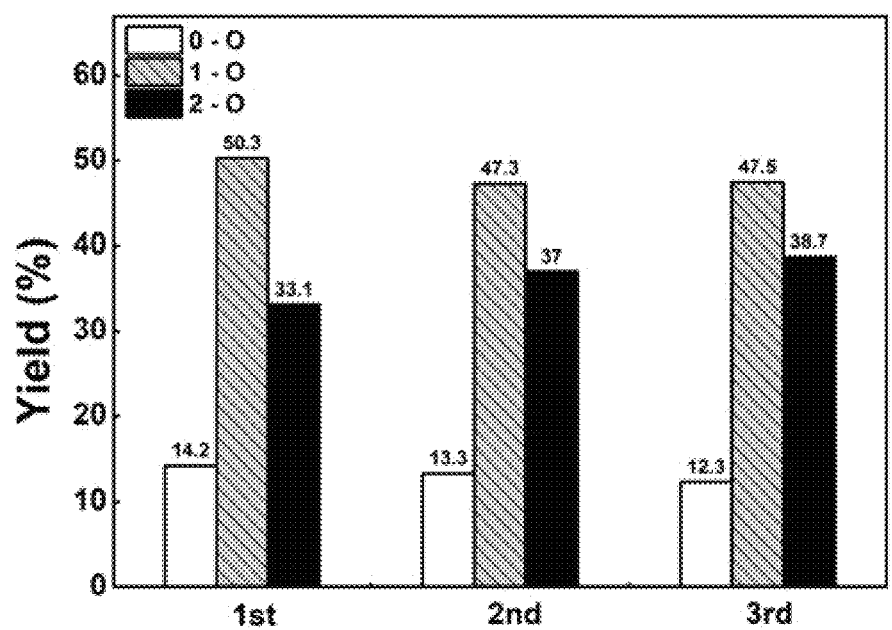
FIG. 4 shows the hydrodeoxygenation reaction results when a hydrodeoxygenation reaction was carried out using a catalyst for hydrodeoxygenation reaction according to one embodiment of the present invention and then the catalyst was washed, dried, and reused.

Also, when the catalyst, after reaction, was washed, dried and reused, the hydrodeoxygenation reaction activity was maintained without a significant change even in the third use of the catalyst, and the hydrodeoxygenation reaction activity was remarkably higher than those of fresh catalysts using a carrier of MgO, Mg—Al mixed oxide ($MgAlO_x$) or hydrotalcite (HT) (see FIG. 4).

While the present invention has been described with respect to the specific embodiments, it will be apparent to those skilled in the art that the above descriptions are only preferred embodiments and that the scope of the present invention is not limited thereto. Thus, the scope of the present invention should be defined by the appended claims and equivalents thereof.

What is claimed is:

1. A catalyst for hydrodeoxygenation reaction comprising at least one carrier selected from the group consisting of calcium chloride, calcium fluoride, calcium hydroxide, calcium nitrate, calcium acetate, calcium citrate, calcium lactate, calcium phosphate, calcium gluconate, calcium sulfate, and calcium iodate, and a metal supported on the carrier, wherein
the metal comprises at least one of nickel (Ni), cobalt (Co), copper (Cu), platinum (Pt), rhodium (Rh), or ruthenium (Ru), wherein the content of the metal is 3% to 15% by weight based on the total weight of the catalyst, and the catalyst removes oxygen atoms from an oxygenate to provide a deoxygenated compound.

2. The catalyst for hydrodeoxygenation reaction according to claim 1, wherein the oxygenate is an oxygen-containing hydrocarbon compounds having 5 to 20 carbon atoms.

3. The catalyst for hydrodeoxygenation reaction according to claim 1, wherein the oxygenate comprises at least one of phenol, alcohol, aldehyde, ketone, ether, or ester.

4. The catalyst for hydrodeoxygenation reaction according to claim 1, wherein the metal comprises ruthenium (Ru).

5. A method for preparing the catalyst for hydrodeoxygenation reaction according to claim 1, comprising the steps of:

(1) mixing a solution of a metal precursor with a carrier comprising a calcium salt to impregnate the carrier with the solution; and (2) firing the carrier impregnated with the solution.

6. The method for preparing the catalyst for hydrodeoxygenation reaction according to claim 5, wherein the firing of the impregnated carrier is carried out in an air atmosphere at 100 to 500° C.

7. A catalyst for hydrodeoxygenation reaction comprising ruthenium (Ru) supported on a carrier selected from the group consisting of calcium chloride, calcium fluoride, calcium hydroxide, calcium nitrate, calcium acetate, calcium citrate, calcium lactate, calcium phosphate, calcium gluconate, calcium sulfate, and calcium iodate, wherein the catalyst removes oxygen atoms from an oxygenate to provide a deoxygenated compound, wherein the oxygenate is a degradation product produced by thermal, chemical or biological degradation of biomass including wood, herbs, or algae, or a degradation product produced from an organic polymer.

8. The catalyst for hydrodeoxygenation reaction according to claim 7, wherein the catalyst does not exhibit a significant change in hydrodeoxygenation reaction activity following two regeneration wash and dry cycles.

\* \* \* \* \*